United States Patent [19]

Reifschneider

[11] 4,361,556

[45] Nov. 30, 1982

[54] METHOD FOR CONTROLLING INSECTS WITH SUBSTITUTED PHENYL PHOSPHOROTHIOATES

[75] Inventor: Walter Reifschneider, Walnut Creek, Calif.

[73] Assignee: The Dow Chemical Company, Midland, Mich.

[21] Appl. No.: 307,961

[22] Filed: Oct. 2, 1981

[51] Int. Cl.$^3$ ...................... C07F 9/165; A01N 57/14
[52] U.S. Cl. ...................... 424/216; 260/949
[58] Field of Search ................ 424/216; 260/949, 946

[56] References Cited

U.S. PATENT DOCUMENTS 3,042,703  7/1962  Schegk et al. ...................... 260/949

FOREIGN PATENT DOCUMENTS 1183494  12/1964  Fed. Rep. of Germany ...... 260/949

OTHER PUBLICATIONS

Unverified translation of Japanese Patent Publication 11880/1966.

Primary Examiner—Anton H. Sutto
Attorney, Agent, or Firm—S. Preston Jones; Ronald G. Brookens

[57] ABSTRACT

0,0-Dimethyl 0-[(4-tert-butylsulfinyl)-2-methoxyphenyl]phosphorothioate and 0,0-dimethyl 0-[(p-tert-amylsulfinyl)phenyl]phosphorothioate are active in the kill and control of black cutworms.

9 Claims, No Drawings

METHOD FOR CONTROLLING INSECTS WITH SUBSTITUTED PHENYL PHOSPHOROTHIOATES

BACKGROUND OF THE INVENTION

Many phosphate and phosphorothioate esters are known to have pesticidal activity of one kind or another. Various related sulfur-substituted phosphorothioate esters are known to be active insecticides and miticides. Among such compounds are the dialkyl alkylsulfinylphenyl phosphorothioates and related esters described in U.S. Pat. No. 3,042,703, West German Pat. No. 1,183,494, and Japanese Pat. No. 11880/66. These patents all disclose esters having the structural formula

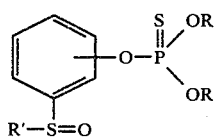

wherein the phenyl group may have one or more inert substituents, R is a lower alkyl group, usually methyl or ethyl, and R' is also a lower alkyl group. These compounds are described in the above patents as active contact insecticides and miticides.

SUMMARY OF THE INVENTION

It has now been found that exceptional and different insecitidal activity exists for the particular compounds O,O-dimethyl O-[(4-tert-butylsulfinyl)-2-methoxyphenyl]phosphorothioate corresponding to the formula

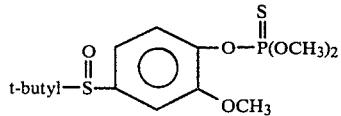

and O,O-dimethyl O-[(p-tertamylsulfinyl)phenyl]phosphorothioate. These compounds corresponding to the formula

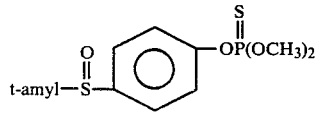

have a tertiary alkyl group in the R' position of the above prior art formula rather than a non-tertiary lower alkyl group as disclosed by said prior art. The present invention comprises the two named compounds, insecticidal formulations containing one or both of said compounds, and the use of such formulations for killing and controlling black cutworms.

DETAILED DESCRIPTION

The compounds of the present invention are useful in agricultural operations, particularly for the kill and control of black cutworms (*Agrotis ipsilon*) which attack the young plants of beans, tomatoes, corn, and other such crops.

When applied to their habitat to protect the plants from the attack of black cutworms, the subject compounds exhibit good residual control of these larvae.

The method of the present invention comprises contacting the larvae or their habitat with an insecticidally effective or inactivating amount of one or both of the compounds of the present invention. The contacting can be effected by application of one or both of the compounds to the larvae or the soil that constitutes their habitat. The inactivation can be lethal, immediately or with delay, or can be a sub-lethal one in which the inactivated insect is not able to carry out one or more of its normal life processes. This latter situation prevails when one of the systems of the insect, typically the nervous system, is seriously disturbed.

The inactivation of an insect by the application of an insecticidally effective or inactivating amount of one or a combination of these compounds is critical to the method of the present invention. These compounds can be employed in unmodified form, or modified by the addition of a pesticidal adjuvant thereto.

Compositions employing one or a combination of these active compounds can be in the form of a liquid or a granulated solid; and the adjuvant employed can be any one of a plurality of materials including aromatic solvents, petroleum distillates, water, or other liquid carriers, surface-active dispersing agents, light absorbers, and granular carrier solids. In such compositions, the adjuvant cooperates with the phosphorus compound so as to obtain a composition to facilitate the method of the present invention, and to obtain an improved result. The use of either a surface-active dispersing agent and a granular carrier solid, simultaneously constitute preferred embodiments of the method of the present invention.

The exact concentration of one or a combination of the compounds of the present invention in a composition thereof with an adjuvant therefor can vary; it is only necessary that one or a combination of the compounds be present in a sufficient amount so as to make possible the application of an insecticidally effective or inactivating dosage. Such a dosage rate is from about 1 to about 100 ppm of dry soil. Generally, for practical applications, the active compound(s) can be broadly applied to black cutworms or their habitat in compositions containing from about 0.00001 percent to about 98 percent by weight of the phosphorus compound(s).

In the preparation of granular compositions, one or a combination of these phosphorus compounds can be compounded with any of carrier solids such as pyrophyllite, diatomaceous earth, gypsum and the like. In such operations, the granular carrier is mixed with the compound(s), as active agent(s) or wetted with a solution of the active agent(s) in a volatile organic solvent. Similarly, granular compositions containing the phosphorus product(s) can be compounded with various solid dispersing agents, such as fuller's earth, attapulgite and other clays. These compositions can be employed as concentrates and subsequently diluted with additional solid dispersing agent or with pyrophyllite, diatomaceous earth, gypsum and the like to obtain the desired amount of active agent in a treating composition.

Furthermore, a compound, a combination of the compounds or a concentrate composition containing such compound(s) can be incorporated in intimate mixture with surface-active dispersing agents such as ionic and nonionic emulsifying agents to form spray concentrates. Such concentrates are readily dispersible in liquid carriers to form sprays contaning the toxicant(s) in any desired amount. The choice of dispersing agent and amount thereof employed are determined by the ability of the agent to facilitate the dispersion of the concentrate in the liquid carrier to produce the desired spray composition.

In the preparation of liquid compositions, the product or a combination of the products can be compounded with a suitable water-immiscible organic liquid and surface active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, one of the products, a combination of products or a composition containing one or both of the products is applied to the soil to be protected directly in any convenient manner, for example, by means of hand spreaders or sprayers. Appliation to the soil on a larger scale is conveniently carried out with power spreaders, boom sprayers and fog sprayers. In large-scale operations, granular compositions or low volume sprays can be applied from an airplane. The present invention also comprehends the employment of compositions comprising one or a combination of these phosphorus compounds, an adjuvant, and one or more biologically active materials, such as other insecticides, fungicides, miticides, bactericides, nematocides, and the like.

The phenolic intermediate for making the compounds of this invention is readily prepared by conventional means. For example, a preferred method comprises reacting 4-mercapto-2-methoxyphenol(4-mercaptoguaiacol) with tertiary butyl alcohol at about 50°–100° C. in inert solvent solution in the presence of sulfuric or phosphoric acid. The 4-tert-butylthio-2-methoxyphenol product is easily isolated by adding water to the reaction mixture and separating the product by conventional means from the organic layer thereby formed. In the same way, p-(tert-amylthio)-phenol is prepared from tert-amyl alcohol and p-mercaptophenol.

This p-(alkythio)phenol product can then be oxidized to the corresponding sulfinyl phenol by reacting it with about a stoichiometric equivalent of any convenient oxidizing agent under mild oxidizing reaction conditions. Suitable oxidizing agents include nitric acid, hydrogen peroxide, and benzoyl peroxide. A mode of oxidation using chlorine water to convert alkylthioaromatics to corresponding alkylsulfinyl compounds is described in U.S. Pat. No. 3,415,832. A more convenient method comprises reacting an equivalent of 30% hydrogen peroxide with the p-(tert-alkylthio)phenol in glacial acetic acid at reflux temperature whereby a good yield of the desired 4-tert-butylsulfinyl-2-methoxyphenol (also named 4-tert-butylsulfinylguaiacol) or the p-(tert-amylsulfinyl)phenol is readily separable from the resulting reaction mixture.

The O,O-dimethyl phosphorochloridothioate reactant is a commercially available material.

The phosphorothioate esters of this invention are readily prepared in high yield as relatively pure products by reacting the substituted sulfinylphenols named above with the phosphorochloridothioate intermediate in inert solvent solution in the presence of an acid acceptor as conventionally used in this type of esterification reaction. Preferred modes of preparation are described in detail in Examples 1 and 2.

EXAMPLE 1

O,O-Dimethyl O-[(4-tert-butylsulfinyl)-2-methoxyphenyl]phosphorothioate

A mixture of 19.4 g of 4-tert-butylsulfinylguaiacol, 13.1 g, of powdered potassium carbonate, 200 ml of acetonitrile, and 13.65 g of O,O-dimethyl phosphorochloridothioate was heated at 50°–55° C. for 4 hours with stirring. After cooling the reaction mixture, precipitated inorganic salts were removed by filtration and the filtrate was concentrated under reduced pressure. The residual oily concentrate (31.8 g) was dissolved in methylene chloride and the solution was washed successively with water, 2% aqueous NaOH, and again with water. The solution was then dried over anhydrous sodium sulfate and the solvent was evaporated off under reduced pressure, leaving a viscous yellow oil, 26.2 g, refractive index at 25° C.=1.5461. The identity of this product was confirmed as the expected O,O-dimethyl O-[(4-tert-butylsulfinyl)-2-methoxyphenyl]-phosphorothioate by nuclear magnetic resonance and elemental analyses.

EXAMPLE 2

O,O-Dimethyl O-[(p-tert-amylsulfinyl)-phenyl]phosphorothioate

A mixture of 21.4 g of p-tert-amylsulfinylphenol, 15.9 g, of powdered potassium carbonate, 200 ml of acetonitrile, and 16.1 g of O,O-dimethyl phosphorochloridothioate was stirred for 5 hours at 60° C. and 2 hours at 70° C. After cooling to room temperature, the reaction mixture was filtered to remove precipitated inorganic salts and the filtrate was concentrated in a rotary evaporator, yielding 34 g of residual yellow viscous oil. This oil was dissolved in benzene and the solution was washed with dilute aqueous NaOH and twice with water. The washed solution was dried over anhydrous sodium sulfate and the benzene was distilled off under reduced pressure. The residue was 22.2 g of a viscous yellow oil, refractive index at 25° C.=1.5525. It was identified as the expected compound named above by nuclear magnetic resonance and elemental analyses.

EXAMPLES 3–4

An aqueous dispersion of predetermined concentration was made up for each of the products of Examples 1 and 2 and similar dispersions of their n-alkyl isomers were also made up using an acetone solution of the compound and a predetermined amount of surfactant. Portions of air-dried soil were put in four glass jars and each portion was treated with one of the dispersions to provide a 25 parts per million concentration of the particular phosphorothioate ester on an air-dry soil basis. Each treated soil sample was well mixed and about a 10 g portion of each treated soil was put in its 8 oz. testing jar. A sample of untreated soil was put in a fifth jar to serve as a control. Each soil portion was moistened with 2 ml of water and an egg sheet containing 25 eggs of the black cutworm was put in each jar. Corn kernels were put in each jar and all jars were closed with a screw top lid, then were allowed to stand for 12 days at room temperature.

At the end of this time, the jars were examined to determine the number of black cutworm larvae on the soil surface, the sprouted seeds, and the soil-jar interface. The results are set forth in Table 1.

TABLE 1

| Compound | % Control of Larvae |
| --- | --- |
| O,O—Dimethyl O—[(4-tert-butylsulfinyl)-2-methoxyphenyl]phosphorothioate | 50 |
| O,O—Dimethyl O—[(4-n-butylsulfinyl)-2-methoxyphenyl]phosphorothioate | 0 |
| O,O—Dimethyl O—[(p-tert-amylsulfinyl)phenyl]phosphorothioate | 100 |
| O,O—Dimethyl O—[(p-n-amylsulfinyl)phenyl]phosphorothioate | 0 |
| None | 0 |

Both compounds of this invention are effective contact miticides, providing good control of two-spotted spider mites when an aqueous dispersion containing 400 ppm of either or a combination of the two is sprayed on them or their habitat. O,O-Dimethyl O-[(4-tert-butylsulfinyl)-2-methoxyphenyl]phosphorothioate is also highly effective when applied similarly to mosquitoes or their habitat in 10 ppm concentration. Similarly, O,O-dimethyl O-[(p-tert-amylsulfinyl)phenyl]phosphorothioate provides good control of such insect pests as tobacco budworm, beet armyworm, and coddling moth larvae when sprayed on them or their habitat as an aqueous dispersion of 200–400 ppm concentration.

I claim:
1. A method for killing and controlling black cutworms which comprises contacting said cutworms or their habitat with a composition containing as an active ingredient an insecticidally effective amount of at least one of O,O-dimethyl O-[(4-tert-butylsulfinyl)-2-methoxyphenyl]phosphorothioate and O,O-dimethyl O-[(p-ter-amylsulfinyl)phenyl]phosphorothioate in intimate admixture with an inert carrier therefor.
2. The method of claim 1 wherein the active ingredient is O,O-dimethyl O-[(4-tert-butylsulfinyl)-2-methoxyphenyl]phosphorothioate.
3. The method of claim 1 wherein the active ingredient is O,O-dimethyl O-[(p-tert-amylsulfinyl)phenyl]phosphorothioate.
4. A compound selected from the group consisting of O,O-dimethyl O-[(4-tert-butylsulfinyl)-2-methoxyphenyl]phosphorothioate and O,O-dimethyl O-[(p-tert-amylsulfinyl)phenyl]phosphorothioate.
5. The compound of claim 4 wherein the compound is O,O-dimethyl O-[(4-tert-butylsulfinyl)-2-methoxyphenyl]phosphorothioate.
6. The compound of claim 4 wherein the compound is O,O-dimethyl O-[(p-tert-amylsulfinyl)phenyl]phosphorothioate.
7. An insecticidal composition comprising as an active ingredient an insecticidally effective amount of at least one of O,O-dimethyl O-[(4-tert-butylsulfinyl)-2-methoxyphenyl]phosphorothioate and O,O-dimethyl O-[(p-tert-amylsulfinyl)phenyl]phosphorothioate in intimate admixture with an inert carrier therefor.
8. The composition of claim 7 wherein the active ingredient is O,O-dimethyl O-[(4-tert-butylsulfinyl)-2-methoxyphenyl]phosphorothioate.
9. The composition of claim 7 wherein the active ingredient is O,O-dimethyl O-[(p-tert-amylsulfinyl)phenyl]phosphorothioate.

* * * * *

UNITED STATES PATENT AND TRADEMARK OFFICE
CERTIFICATE OF CORRECTION

PATENT NO. : 4,361,556
DATED : November 30, 1982
INVENTOR(S) : Walter Reifschneider It is certified that error appears in the above—identified patent and that said Letters Patent is hereby corrected as shown below:

Column 1, line 33, "insecitidal" should read --insecticidal--.

Column 3, line 1, "contaning" should read --containing--.

Column 3, line 30, "Appliation" should read --Application--.

Column 3, line 53, "p-(alkythio)" should read --p-(alkylthio)--.

Column 6, line 8, O-[(p-ter-amylsulfinyl)phenyl] phosphorothioate" should read --O-[(p-tert-amylsulfinyl)phenyl]-phosphorothioate--.

Signed and Sealed this

Twenty-sixth Day of April 1983

[SEAL]

Attest:

GERALD J. MOSSINGHOFF

Attesting Officer

Commissioner of Patents and Trademarks